(12) United States Patent
Ma

(10) Patent No.: US 9,656,259 B2
(45) Date of Patent: *May 23, 2017

(54) AUTO-SUCTION QUANTITATIVE MICRO-BLOOD-SAMPLE COLLECTION TUBE

(71) Applicant: Ronghua Ma, Dongtai (CN)

(72) Inventor: Ronghua Ma, Dongtai (CN)

(73) Assignee: Jiangsu Kehua Medical Instrument Technology Co., Ltd., Dongtai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/433,205

(22) PCT Filed: Jun. 23, 2014

(86) PCT No.: PCT/CN2014/080505
§ 371 (c)(1),
(2) Date: Apr. 2, 2015

(87) PCT Pub. No.: WO2014/173373
PCT Pub. Date: Oct. 30, 2014

(65) Prior Publication Data
US 2015/0251174 A1   Sep. 10, 2015

(30) Foreign Application Priority Data

Apr. 23, 2013   (CN) .......................... 2013 1 0150193

(51) Int. Cl.
*B01L 3/02*   (2006.01)
*A61B 5/15*   (2006.01)

(52) U.S. Cl.
CPC ...... *B01L 3/0293* (2013.01); *A61B 5/150022* (2013.01); *A61B 5/150213* (2013.01);
(Continued)

(58) Field of Classification Search
CPC .... B01L 3/0293; B01L 3/0217; A61B 5/1405; A61B 5/150022; A61B 5/150221
(Continued)

(56) References Cited

U.S. PATENT DOCUMENTS 872,207 A * 11/1907 Dunn .................... B60C 25/147
                                                        157/1
2,728,232 A * 12/1955 Bremmer ................ B01L 3/021
                                                        422/922
(Continued)

FOREIGN PATENT DOCUMENTS

CN     2082154 U    8/1991
CN     2528394 Y    1/2003
(Continued)

OTHER PUBLICATIONS

International Search Report for corresponding International Application No. PCT/CN2014/080505 mailed on Sep. 26, 2014.

*Primary Examiner* — Jill Warden
*Assistant Examiner* — Brittany Fisher
(74) *Attorney, Agent, or Firm* — Billion & Armitage; Benjamin C. Armitage

(57) ABSTRACT

The present invention relates to medical instruments, and particularly to an improved micro-blood-sample collection tube. The auto-suction quantitative micro-blood-sample collection tube of the present invention comprises a micro-blood-sample collection tube which opens at both ends and is of pass-through construction, and a compressible air bag which opens at one end and is hollow. Said micro-blood-sample collection tube is made of hydrophilic material. One end of the micro-blood-sample collection tube is inserted and secured in a port of the air bag, and the inner cavity of the micro-blood-sample collection tube is communicated with the inner cavity of the air bag. The wall of the air bag is provided with a ventilation hole leading to the inner cavity
(Continued)

of said air bag. The present invention does not need hydrophilic treatment, has low cost, highly marketable, and greatly increases the accuracy and efficiency of the blood-sampling process.

5 Claims, 1 Drawing Sheet

(52) U.S. Cl.
CPC ........ *A61B 5/150343* (2013.01); *B01L 3/021* (2013.01); *B01L 2200/0605* (2013.01); *B01L 2300/0838* (2013.01); *B01L 2300/161* (2013.01); *B01L 2400/0406* (2013.01); *B01L 2400/0481* (2013.01)

(58) Field of Classification Search
USPC ........................................ 422/520
See application file for complete search history.

(56) References Cited

U.S. PATENT DOCUMENTS

| | | | |
|---|---|---|---|
| 2,941,869 A * | 6/1960 | Brown | G01N 33/49 422/401 |
| 3,207,156 A * | 9/1965 | Lerman | A61M 1/32 128/DIG. 3 |
| 4,589,421 A | 5/1986 | Ullman | |
| 5,387,204 A * | 2/1995 | Olsson | A61M 1/0007 604/118 |
| 5,775,546 A * | 7/1998 | Buehler | B01L 3/021 222/209 |
| 6,024,138 A | 2/2000 | Fritz et al. | |
| 2008/0140177 A1* | 6/2008 | Hines | A61B 17/12022 623/1.11 |
| 2010/0282263 A1* | 11/2010 | Asada | A62B 11/00 128/206.15 |
| 2011/0129396 A1* | 6/2011 | Fish | B01L 3/022 422/507 |
| 2011/0212482 A1* | 9/2011 | Jangam | A61B 5/1411 435/29 |
| 2012/0160782 A1* | 6/2012 | Yokomizo | A61M 1/3636 210/767 |
| 2014/0186235 A1 | 7/2014 | Kwak et al. | |

FOREIGN PATENT DOCUMENTS

| | | |
|---|---|---|
| CN | 201073303 Y | 6/2008 |
| CN | 201135445 Y | 10/2008 |
| CN | 201182602 Y | 1/2009 |
| CN | 201968685 U | 9/2011 |
| CN | 203169187 U | 9/2013 |
| WO | WO 2014/106092 A1 | 7/2014 |

* cited by examiner

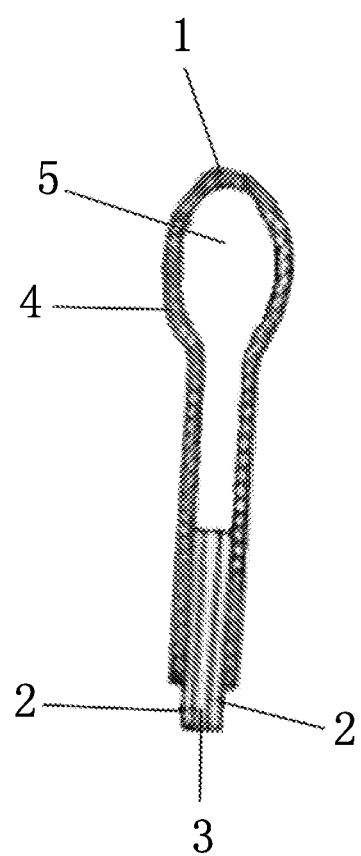

AUTO-SUCTION QUANTITATIVE MICRO-BLOOD-SAMPLE COLLECTION TUBE

CROSS-REFERENCE TO RELATED APPLICATIONS

This application is a National Stage Application of PCT/CN2014/080505, filed on 23 Jun. 2014, which claims benefit of Application No. 201310150193.4, filed on 23 Apr. 2013 in China and which applications are incorporated herein by reference. A claim of priority to all, to the extent appropriate, is made.

TECHNICAL FIELD

The present invention relates to medical instruments, and particularly to an improved a micro-blood-sample collection tube (a micro-volume blood sampling tube).

BACKGROUND ART

A micro-blood-sample collection tube is a commonly used tool for collecting blood in medical departments such as hospitals. Such a micro-blood-sample collection tube is made of a glass tube with small inner diameter, which opens at both ends and is of pass-through construction. One end of the micro-blood-sample collection tube is contacted with the blood to be collected when collecting blood. The blood to be collected is made to enter automatically the interior of the micro-blood-sample collection tube by means of a capillary action. There is generally a requirement for volume when collecting blood, therefore volume scales are marked on the micro-blood-sample collection tube, such as 5 microliters, 10 microliters, 15 microliters, 20 microliters, . . . , 50 microliters. Because the speed at which the blood to be collected enters the micro-blood-sample collection tube is greater, frequently a medical staff does not have enough time to remove the micro-blood-sample collection tube at the moment the blood reaches the required scale, such that actual amount of the collected blood is more than the required amount of the collected blood. Thus, when the blood is removed from the micro-blood-sample collection tube, not only is it necessary to insert the micro-blood-sample collection tube into a latex red dripper and then press the latex red dripper with fingers so as to remove the blood from the micro-blood-sample collection tube, but also necessary to control the removed amount, therefore the whole process takes longer time, and it is inaccurate and inconvenient. An auto-suction micro-blood-sample collection tube made of plastic material is manufactured by a medical instruments manufacturer in US, wherein a micro-blood-sample collection tube and a compressive air bag are made as a whole piece during manufacturing, and ventilation hole(s) is provided at a prescribed scale on tube wall of the micro-blood-sample collection tube. The ventilation hole is clogged with the blood when the blood reaches the prescribed scale, such that the capillary action is stopped, and the blood no longer enters the micro-blood-sample collection tube, so as to complete quantitative micro-volume blood sampling. Then, it is possible to remove the blood by pressing the air bag with fingers. The whole blood-sampling process is accurate, quick and convenient. However, because the auto-suction micro-blood-sample collection tube is made of plastic material, the inner wall of the micro-blood-sample collection tube has hydrophobicity, it is hard for the capillary action to occur to suck blood, thus it is necessary to perform hydrophilic treatment on the inner wall of the plastic micro-blood-sample collection tube during manufacturing. This process takes longer time, with very low production efficiency, which significantly increases product cost and hinders popularization and application of the auto-suction micro-blood-sample collection tubes. So far, low-cost auto-suction micro-blood-sample collection tubes without hydrophilic treatment have not needed to emerge.

DISCLOSURE OF THE INVENTION

In view of the above shortcomings present in the prior art, the technical problem to be solved by the present invention is to provide an auto-suction quantitative micro-blood-sample collection tube, which does not need a hydrophilic treatment, has low-cost, is easy to be popularized and greatly increases accuracy and efficiency of the blood-sampling process.

In order to solve the above mentioned problems, the solution for solving the technical problem of the present invention is to provide an auto-suction quantitative micro-blood-sample collection tube, comprising: a micro-blood-sample collection tube which opens at both ends and is of pass-through construction, and a compressible air bag which opens at one end and is hollow. Said micro-blood-sample collection tube is made of hydrophilic material. One end of the micro-blood-sample collection tube is inserted and secured in the port of the air bag, and the inner cavity of the micro-blood-sample collection tube is communicated with the inner cavity of the air bag. The wall of the air bag is provided with ventilation hole(s) leading to the inner cavity of said air bag.

Using the above mentioned solution, because of the fact that said micro-blood-sample collection tube is made of hydrophilic material, one end of the micro-blood-sample collection tube is inserted and secured in the port of the air bag, and the inner cavity of the micro-blood-sample collection tube is communicated with the inner cavity of the air bag, the air bag is provided with ventilation hole(s) leading to the inner cavity of the air bag, thus the micro-blood-sample collection tube in contact with the blood makes capillary phenomenon occur, and the blood to be collected can easily enter the micro-blood-sample collection tube. When the blood is removed from the micro-blood-sample collection tube, it is possible to block the ventilation hole on the wall of the air bag with fingers and press the air bag. On the other hand, the air bag and the micro-blood-sample collection tube have very low cost, facilitating to promote the popularization, and greatly increase the efficiency and convenience in use.

The volume of the micro-blood-sample collection tube is determined by the product of the cross-section area of the inner cavity of the micro-blood-sample collection tube and the length thereof. Various specific capacity micro-blood-sample collection tubes may be made by selecting properly the inner diameter and length of the micro-blood-sample collection tube (the micro-blood-sample collection tube is generally a circular tube, with the cross-section area of its inner cavity determined by the inner diameter thereof), and the micro-blood-sample collection tubes may be of 5 microliters, 10 microliters, 15 microliters, 20 microliters, . . . , 50 microliters, for example.

The outer wall of the micro-blood-sample collection tube and the inner wall of the port of the air bag are bonded together with glue.

The air bag is flat, facilitating to be secured by fingers during operation.

The air bag is ellipsoidal, facilitating to be secured by fingers during operation.

The ventilation hole is provided at the end portion of the air bag.

The ventilation hole is provided on the bag body of the air bag, such that it is possible to block the ventilation hole with fingers conveniently when pressing the air bag.

The micro-blood-sample collection tube is made of glass.

The micro-blood-sample collection tube is made of hydrophilic polymer material.

BRIEF DESCRIPTION OF DRAWINGS

The auto-suction quantitative micro-blood-sample collection tube of the present invention is further described in detail below by means of the specific embodiments, in conjunction with the drawings.

FIG. 1 is a structural principle schematic diagram of an embodiment of the auto-suction quantitative micro-blood-sample collection tube of the present invention.

DETAILED DESCRIPTION OF EMBODIMENTS

In FIG. 1, the auto-suction quantitative micro-blood-sample collection tube comprises a micro-blood-sample collection tube (2) which opens at both ends and is of pass-through construction and made of glass, and a compressible air bag (1) which opens at one end and is hollow. The micro-blood-sample collection tube (2) is made of glass. One end of the micro-blood-sample collection tube (2) is inserted and secured in the port of the air bag (1), and the inner cavity (3) of the micro-blood-sample collection tube (2) is communicated with the inner cavity (5) of the air bag (1). The wall of the air bag (1) is provided with a ventilation hole (4) leading to the inner cavity (5) of the air bag (1). The ventilation hole (4) may be conveniently blocked with fingers when the air bag is pressed. The outer wall of the micro-blood-sample collection tube (2) and the inner wall of the port of the air bag (1) are bonded together with glue. The air bag (1) is flat, facilitating to be secured by fingers during operation.

The invention claimed is:

1. An auto-suction quantitative micro-blood-sample collection tube, comprising:
    a micro-blood-sample collection tube, configured to open at both ends and is of pass-through construction; and
    a compressible air bag, configured to open at one end and is hollow, with said micro-blood-sample collection tube made of hydrophilic material,
    wherein one end of the micro-blood-sample collection tube is inserted and secured in a port of the air bag, and an inner cavity of the micro-blood-sample collection tube is communicated with an inner cavity of the air bag, and wherein a wall of the air bag is provided with a ventilation hole being free of any objects protruding therefrom and leading to the inner cavity of the air bag, and the air bag is flat without being operated.

2. The auto-suction quantitative micro-blood-sample collection tube according to claim 1, wherein an outer wall of the micro-blood-sample collection tube and an inner wall of the port of the air bag are bonded together with glue.

3. The auto-suction quantitative micro-blood-sample collection tube according to claim 1, wherein the ventilation hole is provided at an end portion of the air bag.

4. The auto-suction quantitative micro-blood-sample collection tube according to claim 1, wherein the micro-blood-sample collection tube is made of glass.

5. The auto-suction quantitative micro-blood-sample collection tube according to claim 1, wherein the micro-blood-sample collection tube is made of hydrophilic polymer material.

* * * * *